(12) United States Patent
Woychik et al.

(10) Patent No.: US 7,451,651 B2
(45) Date of Patent: Nov. 18, 2008

(54) MODULAR SENSOR ASSEMBLY AND METHODS OF FABRICATING THE SAME

(75) Inventors: Charles Gerard Woychik, Niskayuna, NY (US); Rayette Ann Fisher, Niskayuna, NY (US); David Martin Mills, Niskayuna, NY (US); Scott Cogan, Niskayuna, NY (US); David Richard Esler, Mayfield, NY (US); Robert Gideon Wodnicki, Niskayuna, NY (US); Jeffrey Scott Erlbaum, Albany, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/636,822

(22) Filed: Dec. 11, 2006

(65) Prior Publication Data
US 2008/0134793 A1 Jun. 12, 2008

(51) Int. Cl.
*G01N 29/00* (2006.01)
(52) U.S. Cl. ........................................ 73/641
(58) Field of Classification Search ............. None
See application file for complete search history.

(56) References Cited
U.S. PATENT DOCUMENTS
6,551,248 B2   4/2003   Miller et al.
7,309,948 B2 * 12/2007 Kuniyasu et al. ............. 310/334
2003/0013969 A1 * 1/2003 Erikson et al. ............... 600/459
2004/0054287 A1 * 3/2004 Stephens ..................... 600/459
2004/0236223 A1 * 11/2004 Barnes et al. ................ 600/459
2006/0075818 A1 * 4/2006 Huang et al. .................. 73/649
2006/0118939 A1 * 6/2006 Fisher et al. ................. 257/690
2007/0078345 A1 * 4/2007 Mo et al. ..................... 600/459
2007/0113681 A1 * 5/2007 Nishimura et al. ...... 73/862.046
2007/0238993 A1 * 10/2007 Clarke et al. ................. 600/437
2007/0272020 A1 * 11/2007 Schneider et al. ............. 73/628

FOREIGN PATENT DOCUMENTS
WO   WO 2006/018805 A1   2/2006
WO   WO 2006/018806 A1   2/2006

OTHER PUBLICATIONS
U.S. Appl. No. 11/003,602, filed Jun. 08, 2006, Fisher.
K-H Becks et al., A MCM-D type Module for the ATLAS Pixel Detector, 1999, Fraunhofer Institute-IZM, Berlin, Germany.

* cited by examiner

Primary Examiner—Robert R Raevis
(74) Attorney, Agent, or Firm—Fletcher Yoder (57) ABSTRACT

A modular sensor assembly and methods of fabricating a modular sensor assembly are provided. The modular sensor assembly includes a sensor array coupled to an electronics array in a stacked configuration. The sensor array comprises a plurality of sensor modules, each comprising a plurality of sensor sub-arrays. The electronics array comprises a plurality of integrated circuit modules, each comprising a plurality of integrated circuit chips. The sensor modules may be coupled to the electronics modules via flip chip technology.

22 Claims, 6 Drawing Sheets

MODULAR SENSOR ASSEMBLY AND METHODS OF FABRICATING THE SAME

STATEMENT REGARDING FEDERALLY SPONSORED RESEARCH & DEVELOPMENT

This invention was made with Government support under contract number 1 R01 EB002485-01 awarded by the National Institutes of Health. The Government has certain rights in the invention.

BACKGROUND

The present invention relates generally to sensor assemblies and, more specifically, to modular sensor assemblies and methods of fabricating modular sensor assemblies.

Sensor assemblies are typically employed in applications including non-destructive evaluation (NDE) and medical diagnostic imaging, such as ultrasound applications and computed tomography (CT). The sensor assembly generally includes an array of sensors coupled to an electronics array. The sensor array generally includes hundreds or thousands of individual sensors. Similarly, the electronics array includes hundreds or thousands of integrated interface circuits (or "cells") which are electrically coupled to provide electrical control of the sensors for beam forming, signal amplification, control functions, signal processing, etc.

One particular type of widely used sensor is the ultrasonic transducer. Two widely known types of ultrasonic transducers are capacitive micromachined ultrasonic transducers (cMUTs) and piezoelectric transducers (PZT). PZT sensors generally include a piezoelectric ceramic capable of producing electricity when subjected to mechanical stress. cMUT transducers are typically fabricated by forming a flexible membrane disposed over a cavity formed in the silicon substrate. By applying an electrode to the membrane, and to the base of the cavity in the silicon substrate, and applying appropriate voltages across the electrodes, the cMUT may be energized to produce ultrasonic waves. Similarly, when appropriately biased, the membrane of the cMUT may be used to receive ultrasonic signals by capturing reflected ultrasonic energy and transforming the energy into movement of the electrically biased membrane to generate a signal.

Fabricating the sensor array and the electronics array, and coupling the two arrays together, provides a number of design challenges. Semiconductor based sensors are generally fabricated in wafer form and diced, providing a number of sensor chips. PZT sensors are generally fabricated by dicing ceramic block material. Often PZT sensors are formed out of layers of ceramic, matching materials and damping materials. Each sensor sub-array typically includes many sensors. Each sensor sub-array or chip in the sensor array is typically coupled to an integrated circuit chip to provide individual control of each sensor. With hundreds or thousands of sensors and chips, each having countless electrical connections, the fabrication and assembly of such sensor assemblies can be challenging. This challenge becomes amplified when the application calls for size reduction in the sensor assembly. For sensor assemblies that are designed to be used inside the human body, or on small surfaces on the outside of the human body, it is generally desirable to reduce the overall size of the sensor assembly.

One way of reducing the size of the sensor assembly is to place the sensor array on top of the electronics array to provide greater packaging efficiency. However, stacking the sensor array on top of the electronics array introduces a wide variety of design challenges. Further, design, manufacturing and reliability concerns arise when considering the manufacturability of the sensor array, the formation of the sensor assembly, as well as providing a mechanism to cleanly route signals into and out of the sensor assembly.

Embodiments of the present invention may be directed to one or more of the challenges described above.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
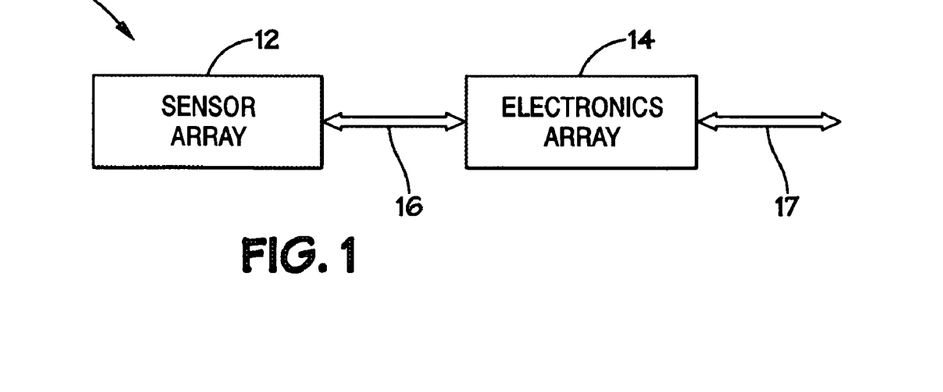
FIG. 1 is a block diagram of a sensor assembly which may be fabricated in accordance with embodiments of the present invention.

Referring initially to FIG. 1, a block diagram of a sensor assembly 10 that may be fabricated in accordance with embodiments of the present invention, is illustrated. The sensor assembly 10 includes a sensor array 12 coupled to an electronics array 14 through an interconnect 16. The sensor array 12 includes a number of individual chips or elements, and each sensor sub-array includes hundreds or thousands of individual sensors. Each sensor may be a PZT element or a cMUT, for example. Alternatively, each sensor may comprise an alternative piezoelectric material, i.e., a single crystal material, such as PMN-PT, a polyvinylidene flouride (PVDF) sensor, a Cadmium Zinc Telluride (CZT) sensor, or a piezoelectric micro machined ultrasonic transducer (PMUT). The electronics array 14 includes a number of integrated circuit (IC) chips configured to control the sensor array 12 and/or to process signals received from the sensor array. The interconnect 16 generally provides an electrical interface between the sensor array 12 and the electronics array 14. Further, in accordance with embodiments of the present invention, because the sensor array 12 and the electronics array 14 are arranged in a stacked configuration, the interconnect 16 may also provide a mechanical interface between the sensor array 12 and the electronics array 14, as will be described further below. The sensor assembly 10 may be coupled to a system (not shown) through an interface 17. The interface 17 is configured to provide a bi-directional signal path to route signals and sensor information between the sensor assembly 10 and a sensor system, such as an ultrasound system.

In accordance with embodiments of the present invention, there is generally a 1-to-1 correspondence between sensor sub-arrays and IC chips. That is to say that there is generally one IC chip for each sensor sub-array in the sensor assembly 10. The sensor sub-array to IC chip ratio may be something other than 1-to-1 (e.g., 2:1, 3:1, etc.). Regardless, the sensor assembly 10 includes a plurality of individual sensor sub-arrays and a plurality of individual IC chips for controlling the sensor sub-arrays and/or processing the receive signals. The relationship of the sensor sub-arrays to the IC chips will be described in detail below.

Figure 2:
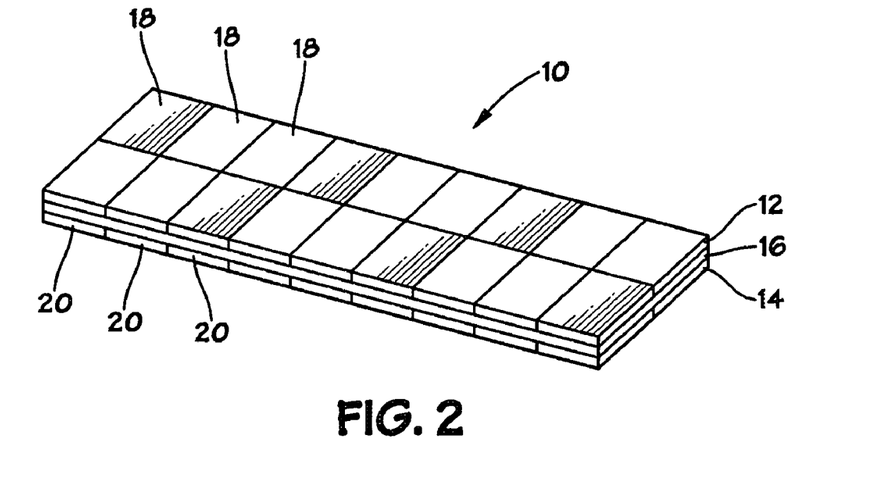
FIG. 2 is a plan view of a modular sensor assembly which may be fabricated in accordance with embodiments of the present invention.

Referring now to FIG. 2, a plan view of the sensor assembly 10 of FIG. 1 is illustrated. As described above, the sensor assembly 10 is generally coupled to a system, such as an ultrasound or CT system which may include a number of drivers, transmitters, receivers, signal processors, converters, switching networks, memory devices, user interfaces and video monitors, for instance. For simplicity, these additional system elements, as well as the interconnect wires/cables from the sensor assembly 10 to the system, have been omitted from FIG. 2. However, those skilled in the art will appreciate the additional elements that may be employed in an ultrasound or CT system.

Referring again to FIG. 2, the sensor array 12 is stacked on top of the electronics array 14. The interconnect 16 provides electrical and mechanical coupling between the sensor array 12 and the electronics array 14. In accordance with one exemplary embodiment, the sensor array 12 is coupled to the electronics array 14 via flip chip technology, and the interconnect 16 includes a plurality of conductive bumps. The interconnect 16 will be described further below with respect of FIGS. 7 and 13. The presently illustrated sensor array 12 includes two rows of sensor sub-arrays 18, each having many sensors (not shown). As previously described, the electronics array 14 also includes a plurality of individual IC chips 20. In accordance with one exemplary embodiment, there is one IC chip 20 corresponding to each sensor sub-array 18.

Further, while the sensor assembly 10 illustrated in FIG. 2 illustrates a single sensor array 12 coupled to a single electronics array 14, other stacked configurations are possible, in accordance with embodiments of the present invention. In one exemplary embodiment, a second sensor array (not shown) may be coupled to the other side of the electronics array 14, via a second interconnect (not shown). In this arrangement, the stack would include an electronics array sandwiched between two sensor arrays, wherein each sensor array is coupled to a respective side of the electronics array via a respective interconnect. In another embodiment, a second electronics array may be included. In this embodiment, another sensor assembly 10, substantially the same as the sensor assembly 10 illustrated in FIG. 2, may be coupled to the backside of the electronics array 14 of FIG. 2. That is, two sensor assemblies 10 may be stacked together to create a stack including two electronics arrays, coupled back to back and sandwiched between two sensor arrays, wherein each of the sensor arrays is coupled to a respective one of the electronics arrays via a respective interconnect.

In accordance with embodiments of the present invention, the sensor assembly 10 is entirely "modular." That is, the sensor array 12 and the electronics array 14 are manufactured in modules. More specifically, the sensor array 12 includes a number of sensor modules, wherein each sensor module includes a number of sensor sub-arrays 18. Similarly, the electronics array 14 includes a number of IC modules, wherein each IC module includes a number of IC chips 20. The number of sensor sub-arrays 18 in each sensor module and the number of IC chips 20 in each IC module may be chosen to optimize manufacturability, reliability and/or electrical performance, for example. Further, in accordance with embodiments of the present invention, the IC modules and sensor modules are fabricated independently of one another. Once each module is fabricated and tested, the sensor modules and IC modules may be coupled together, as will be described further below. This modularity further extends to the coupled sensor module and IC module grouping and allows larger arrays to be built by placing these sensor/IC grouping "modules" next to each other. These modules may also be tested as a group and replaced in a working array assembly, if they are later determined to be bad or have failed in the field, without having to dispose of the entire array.

Figure 3:
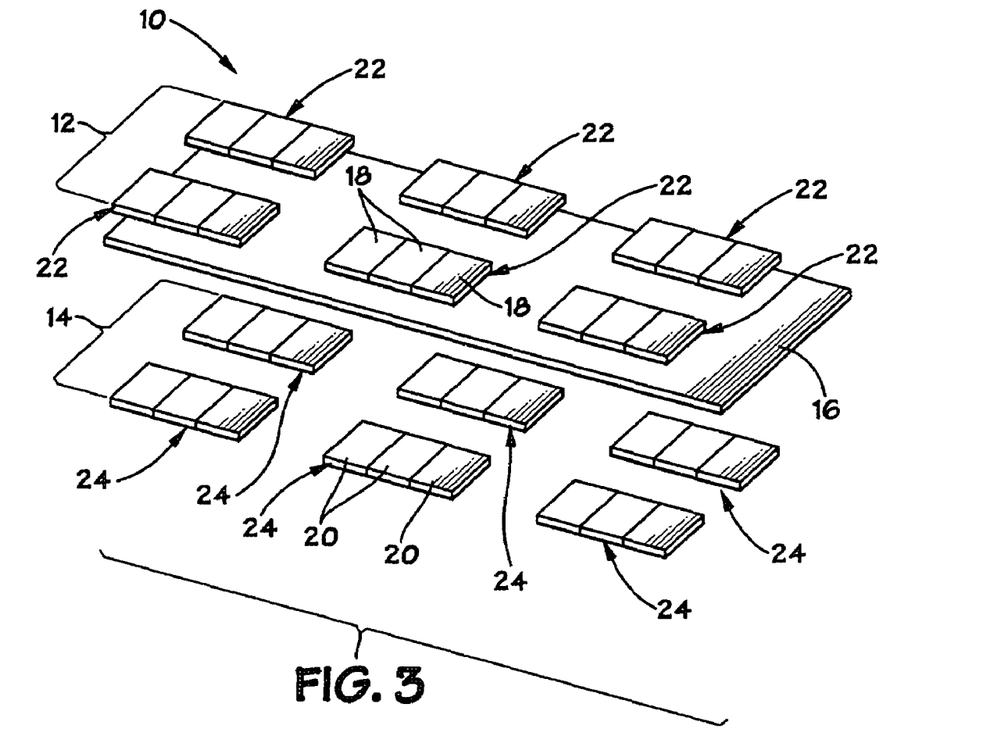
FIG. 3 is an exploded view of the modular sensor assembly illustrated in FIG. 2.

Turning now to FIG. 3, an exploded view of an exemplary embodiment of the sensor assembly 10 is illustrated. For illustrative purposes, the interconnect 16 illustrated in FIG. 3 is simply depicted as a solid sheet. However, as will be described further below with regard to FIGS. 7 and 13, the interconnect 16 may comprise a number of individual interconnects, such as conductive bumps on one or both of the sensor sub-arrays 18 and IC chips 20, which may be coupled by reflowing the bumps. Accordingly, the interconnect 16 of FIG. 3 is illustrated as a single sheet for convenience and simplicity. Those skilled in the art will appreciate the various types of interconnects that may be employed, several of which are described in more detail below. The embodiment illustrated in FIG. 3 includes six (6) sensor modules 22. Each sensor module 22 includes three sensor sub-arrays 18, each arranged adjacent to one another. Accordingly, each sensor module 22 is a "3×1 module" (three sensor sub-arrays arranged in one row). The number of sensor sub-arrays 18 in each sensor module 22 may vary depending on the specific application and the fabrication capabilities of the manufacturer. A further consideration may be the reliability and robustness of each of the sensor sub-arrays 18. The more robust and reliable the sensor sub-array 18 after dicing a wafer to form the sensor module 22, the larger the sensor module 22 may be. If a manufacturer is concerned with failure of a single sensor sub-array 18, the manufacturer may choose to reduce the number of good sensor sub-arrays 18 that may have to be scrapped due to the failure of one of the sensor sub-arrays 18 in the sensor module 22 by minimizing the size of the sensor module 22. As used herein, a "module" refers to a grouping of chips or devices (here sensor sub-arrays 18) which are not separated from one another or diced at any point during fabrication.

In accordance with further embodiments of the present invention, the electronics array 14 is also modular. The electronics array 14 includes a number of IC modules 24. Each IC module includes a number of IC chips 20. In the presently illustrated embodiment, each of the IC modules 24 is also a 3×1 module. That is, each IC module 24 includes three IC chips 20 arranged adjacent to one another in a single row. As with the number of sensor sub-arrays 18 in each sensor module 22, the number of IC chips 20 in each IC module 24 may be chosen to optimize manufacturability, reliability and/or electrical performance.

By fabricating and testing the IC modules 24 and the sensor modules 22 independently of one another, advances or limitations in the technologies employed to fabricate the different types of modules (sensor or IC) will not affect the other. For instance, for the IC modules 24 which may be fabricated employing standard CMOS technology, advances in CMOS technology or limitations therein, will not have an impact on the fabrication of the sensor modules 22. Similarly, advances or limitations in the fabrication of the sensor modules 22 will not adversely impact fabrication of the IC modules. Further, the ability to test and scrap each of the types of modules before forming the sensor assembly by coupling the modules to one another through the interconnect 16 may reduce rework and minimize the amount of scrap due to assembly failures. The interconnect 16 may be implemented on a modular basis alone, a single IC to sensor sub-array alone, or for the entire array simultaneously.

Further, depending on the type of interconnect technology employed, the modular design of the sensor assembly 10 may facilitate rework of the sensor assembly 10 while minimizing the amount of scrap due to failures. For instance, after the assembly is complete and the sensor modules 22 are coupled to the IC modules 24, if there is a failure in a single sensor sub-array 18, the sensor module 22 including the failed sensor sub-array 18 may be replaced. Advantageously, replacing a single sensor module 22 will only result in the scrapping of a minimum number of functional sensor sub-arrays (i.e., those included in the module containing the failed element). Thus, the IC chips 20 coupled to the failed sensor module 22, as well as the remaining sensor modules 22, need not be replaced. If the interconnect technology does not lend itself to disconnection of a sensor module 22 from the IC module 24 after assembly to allow for replacement of a failed module, the amount of waste resulting from the scrapping of good devices coupled to the failed element is also minimized, because only the IC chips 20 in the IC module 24 coupled to the sensor module 22 having the failed sensor sub-array 18 will be scrapped. This may be especially convenient in systems having a 1:1 ratio of sensor modules 22 to IC modules 24. Since the electronics array 14 is also modular, the same advantages will also apply to failures of individual IC chips 20.

Figure 4:
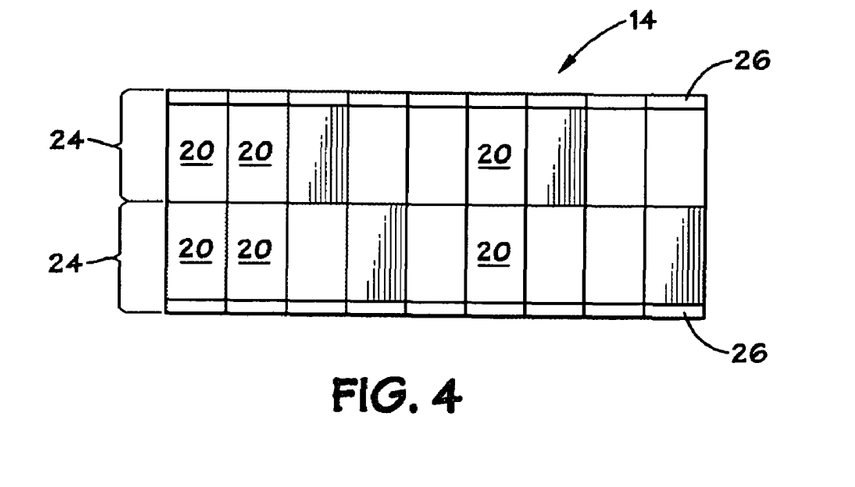
FIG. 4 is a top plan view of a portion of an electronics array that may be fabricated in accordance with embodiments of the present invention.

FIG. 4 illustrates a top plan view of an exemplary electronics array 14. The electronics array 14 of FIG. 4 includes two 9×1 IC modules 24. That is, each IC module 24 includes nine IC chips 20 arranged adjacent to one another in one row. As previously described, the number of IC chips 20 in the IC modules 24 may vary depending on a number of variables described above. Accordingly, each IC module 24 may be N chips wide, where N is the number of IC chips 20. In the present example, N=9. Advantageously, and in accordance with further embodiments of the present invention, each IC chip 20 includes an I/O pad region 26 for coupling each IC chip 20 (and corresponding sensor sub-array 18) to a system, such as an ultrasound system (not shown). Advantageously, the I/O pad region 26 may be arranged along a single edge of each IC chip 20, as illustrated in FIG. 4. Alternatively, each IC chip 20 may include more than one I/O pad regions arranged along more than one edge. In accordance with one exemplary embodiment, the I/O pad region 26 may be coupled to a flex cable, as will be described in greater detail with reference to FIG. 7. Further, it may be possible to form I/C modules 24 which include more than one row (e.g., a 3×2 IC module 24), depending on the I/O configuration. The size of each IC chip 20 is such that each corresponding sensor sub-array 18 that will eventually be stacked on top of the IC chip 20 is substantially the same size as the IC chip 20, not including the I/O pad region 26. That is, once the sensor array 12 is coupled to the electronics array 14, the I/O pad region 26 of each IC chip 20 may extend beyond the footprint of the overlying sensor sub-array 18. Alternatively, through-wafer vias may be employed to route the I/O pad signals from the electronics array 14 to the top of the sensor array 12 where they can be wire-bonded or connected directly to a flex assembly, as will be described and illustrated further below.

Figure 5:
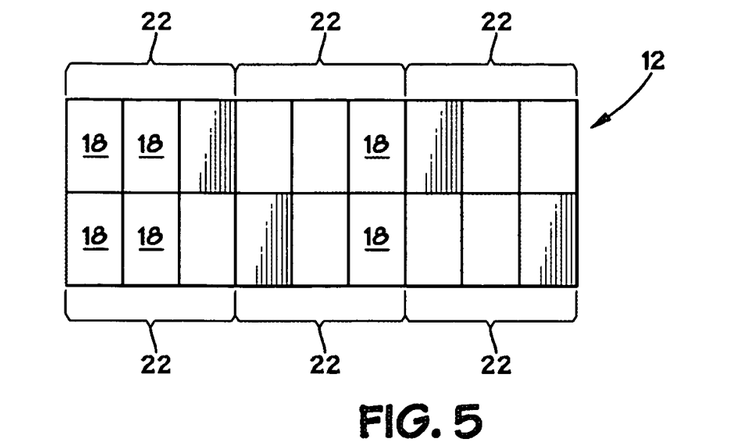
FIG. 5 is a top plan view of a portion of the sensor array which may be fabricated in accordance with embodiments of the present invention.

FIG. 5 illustrates a top plan view of an exemplary sensor array 12. The sensor array 12 of FIG. 5 may comprise six 3×1 sensor modules 22. That is, each sensor module 22 comprises three sensor sub-arrays 18 arranged adjacent to one another in one row. The number of sensor sub-arrays 18 in each sensor module 22 may vary. Accordingly, each sensor module 22 may be M sensor sub-arrays wide, wherein M is the number of sensor sub-arrays 18. In the present example, M=3. Further, it may be possible to employ sensor sub-arrays 18 which include more than one row (e.g., a 3×2 sensor sub-arrays 18), depending on the I/O configuration. As previously described, the sensor array 12, illustrated in FIG. 5 and comprising six, 3×1 sensor modules 22, could be coupled to a similarly configured electronics array 14 comprising six, 3×1 IC modules 24. That is, there may be a 1:1 correspondence of the sensor modules 22 to the IC modules 24. However, depending on the advantages of employing various arrangements of modules, the ratio may be different. For instance, the sensor array 12 of FIG. 5 comprising six, 3×1 sensor modules 22, may be coupled to the electronics array 14 of FIG. 4, comprising two, 9×1 IC modules. In this exemplary sensor assembly 10 configuration, combining the electronics array 14 of FIG. 4 and the sensor array 12 of FIG. 5, the ratio of sensor module 22 to electronics module 24 will be 3:1, rather than 1:1.

Figure 6:
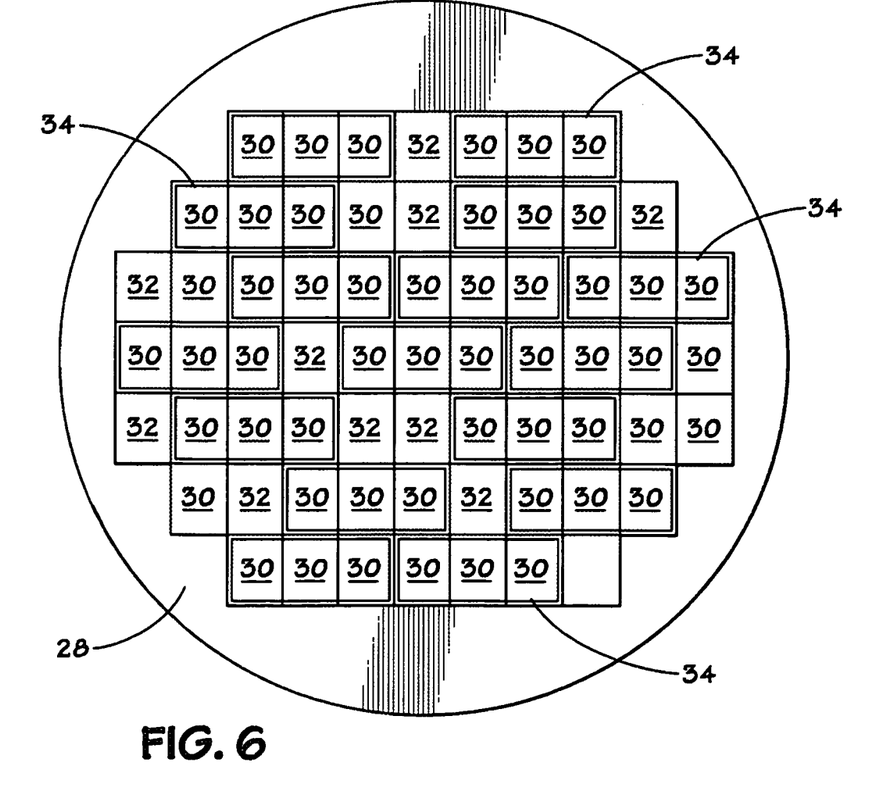
FIG. 6 is a top plan view of a wafer of individual sensor arrays or individual Integrated Circuit (IC) electronic devices which may be diced to form sensor modules or electronics modules in accordance with embodiments of the present invention.

Turning now to FIG. 6, one of the advantages of embodiments of the present invention may be described by referring to a top plan view of a wafer 28 having a plurality of die fabricated thereon. The die may comprise either sensor sub-arrays 18 or IC chips 20, for example. The die may be tested for electrical functionality to identify good die 30 and bad die 32. Rather than determining a particular scribe pattern before electrical testing, by pre-determining which die will make up a particular module after dicing, the scribe pattern can be determined once the electrically good die 30 have been identified. Determining the scribe pattern after electrical testing, results in identification of the maximum number of electrically good modules 34 based on the location of the electrically good die 30 on the wafer 28. As indicated in FIG. 6, after each of the electrically good die 30 have been identified, the scribe pattern can be determined so as to maximize the number of electrically good modules 34. In the present example, each module 34 (indicated by thickened lines) includes three electrically good die 30. In accordance with the illustration of FIG. 6, sixteen (16) electrically good modules 34 may be produced. This concept may be applied to the fabrication of the sensor modules 22, the IC modules 24, or to both. Accordingly, modules 34 having known good die 30 may be employed to fabricate the sensor assembly 10. Independent determination of sensor and electronics array yields, produces a combined yield that is higher than what might have been achieved if the two fabrication processes were combined.

Figure 7:
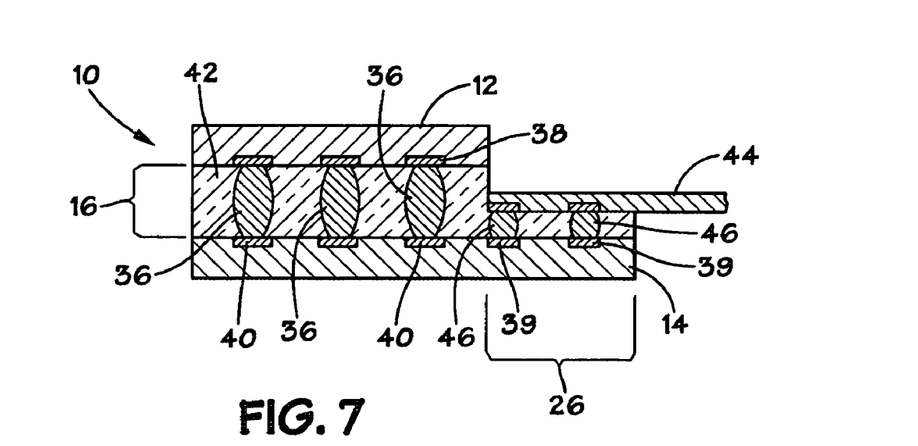
FIGS. 7-12 are cross-sectional views illustrating alternate embodiments of the interconnection between a sensor array and an electronics array and the interconnection between the sensor assembly and a system, in accordance with exemplary embodiments of the present invention.
Figure 8:
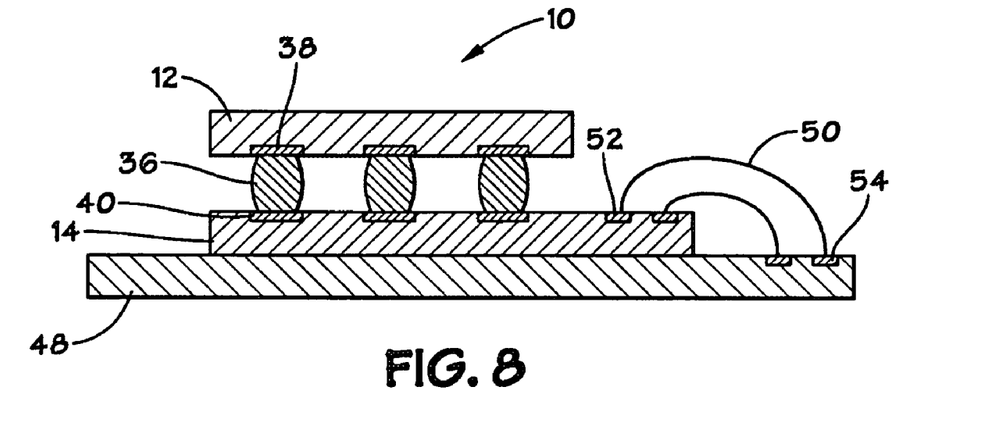

Referring now to FIG. 7, a cross-sectional side view of a portion of the sensor assembly 10 illustrating an exemplary embodiment of the interconnection of the electronics array 14 to the sensor array 12 and to the system is provided. As illustrated in FIG. 7, the sensor array 12 may be coupled to the electronics array 14 using flip chip technology. As will be described in more detail with reference to FIG. 13, the sensor array 12 may be coupled to the electronics array 14 by conductive bumps 36. The conductive bumps 36 form the electrical interconnection between the electronics array 14 and the sensor array 12. In accordance with the exemplary embodiment of FIG. 7, the sensor array 12 and the electronics array 14 each include conductive pads 38 and 40, respectively. As used herein, "flip chip technology" includes any technique wherein electrically conductive material is disposed on the conductive pads 38 or the conductive pads 40, or both, and the material is then used to electrically and/or mechanically couple the sensor array 12 to the electronics array 14. Accordingly, while the embodiment described and illustrated with reference to FIGS. 7-13 includes the deposition of conductive metals to form metal bumps on the conductive pads 38 and/or 40, a combination of metal and non-metal may be employed (e.g., gold stud bumps having conductive epoxy bumps formed thereon) may be employed. Alternatively, rather than bumping, an anisotropic conductive film maybe disposed over the backside of the sensor array 12 and the conductive pads 38 and/or disposed over the backside of the electronics array 14 and the pads 40, to couple the arrays together via flip chip technology.

The interconnect 16 may also include an underfill material 42, which could be either a conventional capillary underfill, or a no-flow underfill that has the feature of a "fluxing epoxy," that may be disposed or injected between the sensor array 12 and the electronics array 14. Alternatively, the underfill material 42 may comprise a solid preform that may be disposed onto the electronics array 14, before coupling the electronics array 14 to the sensor array, or vice versa. In this embodiment, apertures may be formed through the preform to create openings which align with the conductive pads 38/40, that are configured to receive deposition of the bumping material. In certain embodiments, the underfill material may also comprise or include materials having desirable acoustical properties or materials that are thermally loaded for better electrical and mechanical performance. The height of the interconnect 16 may also be adjusted to provide specific acoustic performance, such as to provide good acoustical matching or transfer of energy between the sensor array 12 and the electronics array 14 or to provide significant damping of the acoustical energy from the back for the sensor array 12. Alternatively, the underfill material 42 may be omitted.

As previously described, each IC chip of the electronics array 14 includes an I/O pad region 26 having I/O pads 39 for electrically coupling the corresponding IC chip and sensor sub-array to a system (such as an ultrasound system). In accordance with one exemplary embodiment, the I/O pad region 26 also includes conductive bumps 46 which may be used to route signals to and from the sensor assembly 10 through a transmission medium, such as a flex cable 44. Because the I/O pad region 26 is arranged along a single side of each IC chip and because the I/O pad region 26 extends beyond the footprint of the overlying sensor array 12, easy electrical access to and from the sensor assembly 10 is provided. Solder reflow is used to create connections between the sensor array 12 and the electronics array 14 by melting the conductive bumps 36. This process is self-aligning and therefore facilitates registration of the sensor and electronics arrays. While the exemplary illustration of FIG. 7 shows conductive bumps 36 as being larger than the conductive bumps 46, it should be understood that in certain embodiments, the conductive bumps 36 may be smaller than the conductive bumps 46, or may be approximately the same size as conductive bumps 46. Also, in certain embodiments, the bumps in the I/O pad region 26 may be of a different size, different material and/or have different reflow properties compared to the bumps in the interconnect region 16. Further, while the illustrated embodiment provides an I/O pad region 26 on the electronics array 14 and the flex cable 44 is coupled thereto, an I/O pad region may instead be fabricated on the sensor array 12 such that the flex cable 44 may be attached to electrically couple the sensor assembly 10 to a system.

FIGS. 8-12 illustrate cross-sectional views of alternate embodiments of the sensor assembly 10, employing different configurations and mechanisms for mechanically and electrically coupling the sensor array 12 to the electronics array 14 and/or for coupling the sensor assembly 10 to a system. For instance, in accordance with the embodiment illustrated in FIG. 8, the sensor array 12 is coupled to the electronics array via conductive bumps 36, as previously described with reference to FIG. 7. However, rather than electrically coupling the electronics array 14 to a system via conductive bumps 46 coupled to a flex cable 44, as in FIG. 7, the electronics array 14 is mechanically coupled to a substrate 48, via epoxy, paste or glue, for example. The substrate 48 may comprise a printed circuit board, ceramic, flex, rigid flex or FR4, for example. The electronics array 14 (and thus the entire sensor assembly 10) is electrically coupled to the substrate 48 via bondwires 50. As will be appreciated, in accordance with this embodiment, the I/O region 26 of the electronics array 14 includes wirebond pads 52 to electrically couple bondwires. The substrate 48 also comprises wirebond pads 54 and conductive routing (not shown) through the substrate 48 such that the substrate 48 can be used to couple the sensor array 10 to a system. Though not shown, the area between the sensor array 12 and the electronics array 14 may also include an underfill material, as previously described with reference to the underfill material 42 of FIG. 7.

Figure 9:
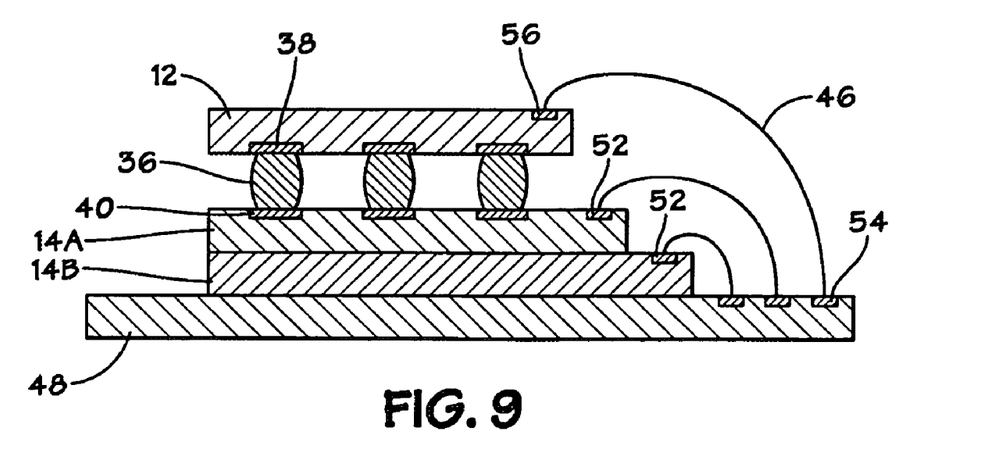

FIG. 9 illustrates a cross-sectional view of another alternate embodiment of the sensor assembly 10. In accordance with the embodiment of FIG. 9, the sensor assembly 10 includes a first electronics array 14A and a second electronics array 14B. The sensor array 12 is coupled to the first electronics array 14A via conductive bumps 36. The first electronics array 14A is mechanically coupled to the second electronics array 14B via epoxy, paste, glue, or via a direct mechanical bond (e.g., a fusion bond, an atomic bond, or a compressive bond). The second electronics array 14B is coupled to a substrate 48 via epoxy, paste, or glue. Each of the electronics arrays 14A and 14B are electrically coupled to the substrate 44 via bond wires 50. In the illustrated embodiment, the sensor array 12 is also electrically coupled to the substrate 44 via bond wires 50. Accordingly, the sensor array 12 also includes bond wire pads 56. Alternatively, the sensor array 12 may be electrically coupled to the first electronics array 14A through the conductive bumps 36 and the signals from the sensor array 12 may then be routed to the substrate 48 via bond wires 50 from the first electronics array 14A. Though not shown, the sensor array 12 and the first electronics array 14A may also include underfill material, as previously described with reference to the underfill material 42 of FIG. 7.

Figure 10:
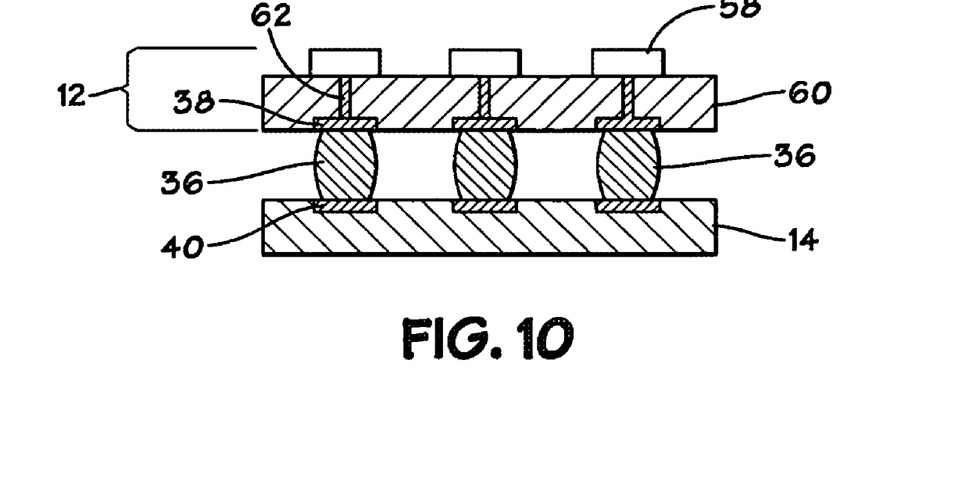
Figure 11:
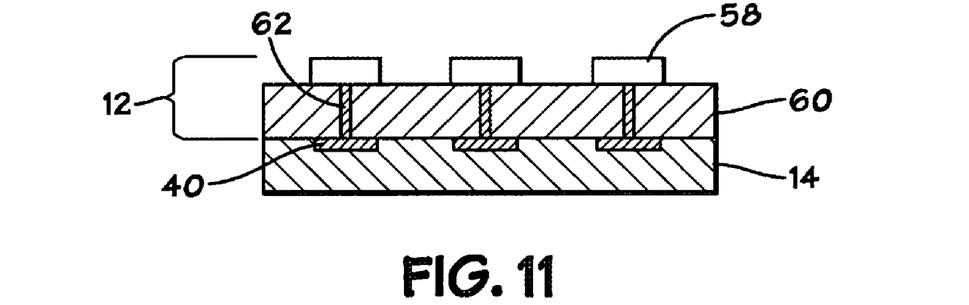
Figure 12:
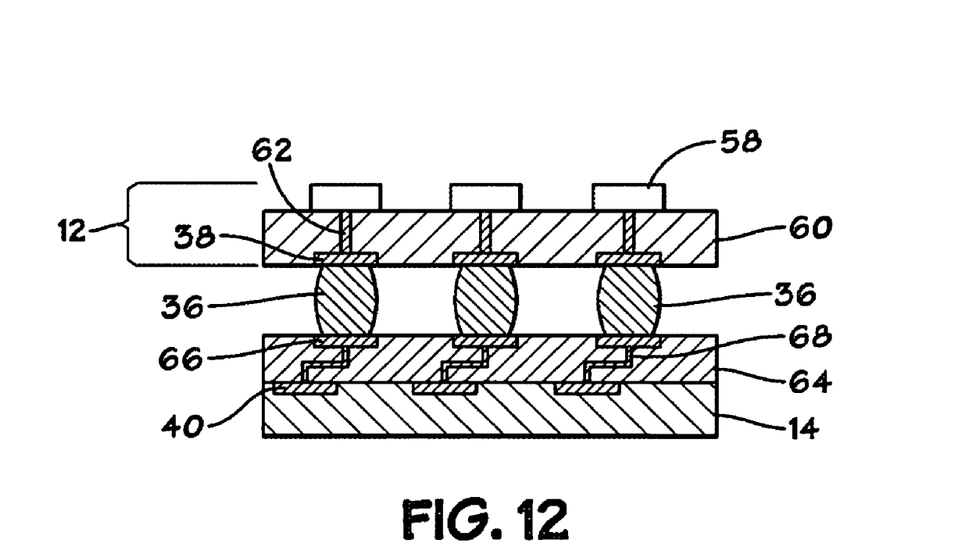

FIGS. 10-12 illustrate alternate embodiments of coupling the sensor array 12 to the electronics array 14, using through wafer vias. Specifically, FIG. 10 illustrates a cross-sectional view of another alternate embodiment of the sensor assembly 10, employing through wafer vias. In accordance with the embodiment of FIG. 10, the sensor array 12 is fabricated such that the active sensors 58 are fabricated on one side of a wafer 60. Through-wafer vias 62 which are filled with a conductive material, such as a metal, are formed through the wafer 60 of the sensor array 12 to electrically couple the sensor 58 to pads 38 on the backside of the wafer 60. The sensor array 12 is electrically coupled to the electronics array 14 via conductive bumps 36, as previously described. Though not shown, the sensor array 12 and the first electronics array 14A may also include underfill material therebetween, as previously described with reference to the underfill material 42 of FIG. 7.

FIG. 11 illustrates a cross-sectional view of yet another alternate embodiment of the sensor assembly 10, employing through wafer vias. In accordance with the embodiment of FIG. 1, the sensor array 12 is fabricated such that the active sensors 58 are fabricated on one side of a wafer 60 having through wafer vias 62, as described with reference to FIG. 10. However, instead of employing conductive bumps 36 to electrically couple the sensor array 12 to the electronics array 14, as in FIG. 10, the sensor array 12 is coupled directly to the electronics array 14. The vias 62 are electrically coupled to the pads 40 on the electronics array 14, thereby providing a signal path.

FIG. 12 illustrates a cross-sectional view of yet another alternate embodiment of the sensor assembly 10 employing through wafer vias. In accordance with the embodiment of FIG. 12, rather than coupling the sensors 58 to the electronics array 14 by directly coupling pads 38 on the sensor array 12 to pads 40 on the electronics array through conductive bumps 36 positioned therebetween, as in the embodiment of FIG. 10, a redistribution layer (RDL) 64 on top of the electronics array 14 is employed. The RDL layer 64 includes pads 66 to couple the RDL 64 to the conductive bumps 36. The RDL 64 also includes conductive paths 68 formed therethrough and coupled to the pads 40 of the electronics array 14. By incorporating an RDL layer 64 on the electronics array 14, the pads 38 of the sensor array 12 and the pads 40 of the electronics array 14 do not need to be aligned since the RDL layer 64 will be configured to provide the electrical connection therebetween. In alternate embodiments, the sensor array 12 may have an RDL layer in addition to or instead of the RDL layer 64 on the electronics array 14.

Figure 13:
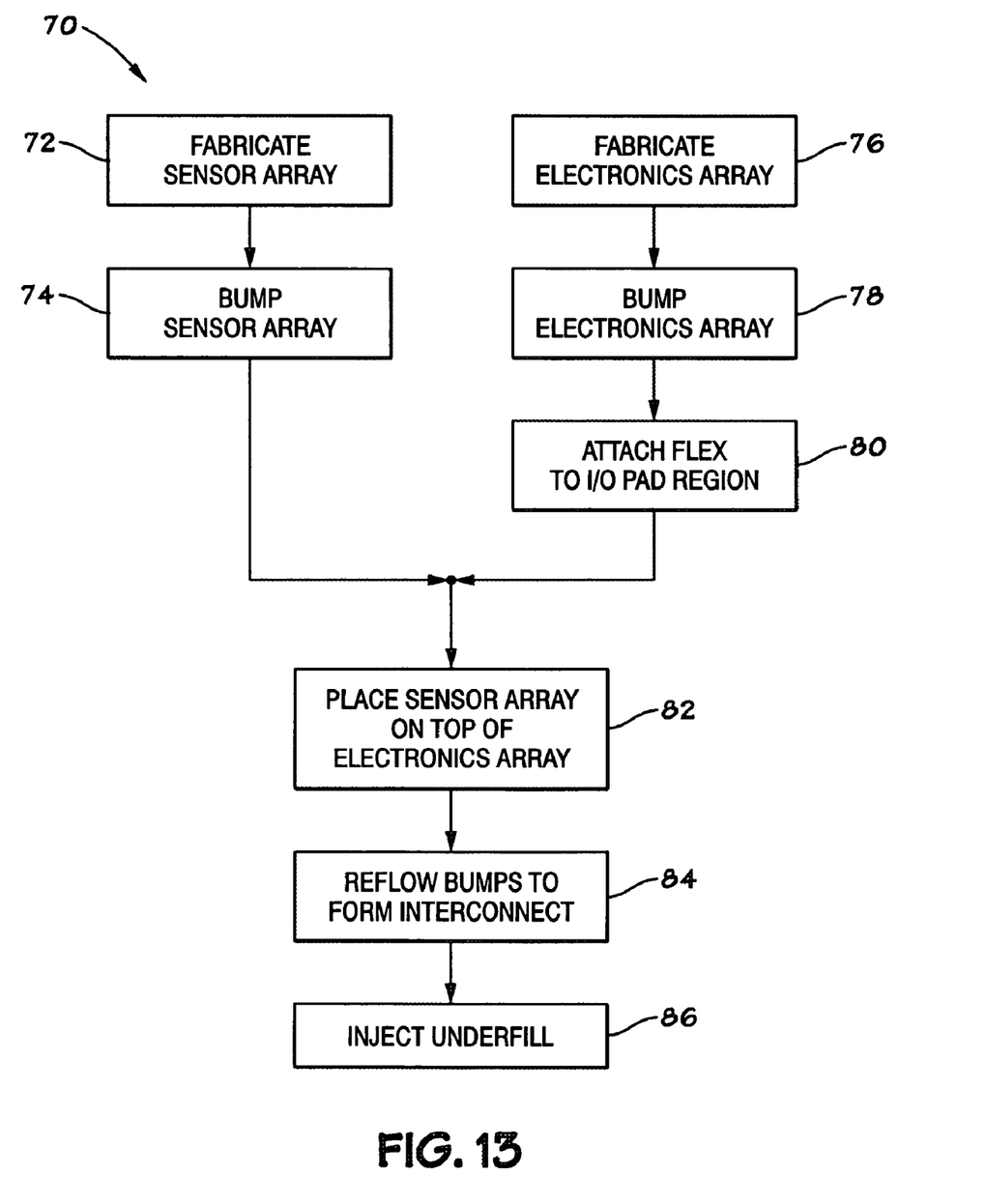
FIG. 13 is a flow chart describing a method of fabricating a sensor assembly in accordance with embodiments of the present invention.

Turning now to FIG. 13, a flow chart illustrating an exemplary process 70 for fabricating a sensor assembly 10 in accordance with embodiments of the present invention is illustrated. The process 70 is specifically directed to fabricating the embodiment illustrated and described with respect to FIG. 7. Accordingly, the process 70 will be best understood with cross-reference to FIG. 7. Those skilled in the art will appreciate and understand the variations in the process 70 necessary in order to fabricate the various embodiments illustrated with regard to FIGS. 8-12.

As previously described, the sensor array 12 and the electronics array 14 are fabricated independently of each other. Accordingly, the sensor array 12 and the electronics array 14 may be fabricated simultaneously. The sensor array 12 is fabricated, as indicated in block 72. At this point in the process, the fabricated sensor array 12, as well as the electronics array 14, can be tested to determine those die with known-good yield. After fabrication and before dicing the modules, electrically conductive bumps are coupled to pads 38 on the backside of the sensor array 12, as indicated in block 74. The processing of the sensor array 12 generally includes depositing an under-bump metallurgy (UBM) on the conductive pads 38 on the backside of the sensor array 12 (i.e., "bumping" the conductive pads 38). In one exemplary embodiment, the UBM is composed of titanium-nickel-copper. After the UBM is deposited, a protective layer, such as a gold layer may be deposited on the UBM layer. Similarly, after the electronics array 14 is fabricated, as shown in block 76, electrically conductive bumps may be deposited on conductive pads 40 on the backside of the electronics array 14, as indicated in block 78. In one embodiment, a UBM layer, such as titanium-nickel-copper, is deposited on each of the pads 40, including those in the I/O pad region 26. Next, a solder alloy layer, such as eutectic tin-lead or a lead-free tin-silver-copper alloy, is deposited on the UBM layer of the electronics array 14. As will be appreciated, other materials may be employed to bump the sensor array 12 and/or the electronics array 14, including, but not limited to, lead-free tin or silver. Since the interconnection of the electronics array 14 to the sensor array 12 is different than the interconnection between the electronics array 14 and the flex cable 44 (FIG. 7), the pads in the I/O pad region 26 may be bumped differently. That is, the bumps in the I/O pad region 26 may be of a different size, different material and have different reflow properties compared to the bumps in the interconnect region 16. In one exemplary embodiment, after deposition of the UBM layer on the pads 39 in the I/O pad region 26, a gold layer is deposited onto the UBM layer on the pads in the I/O pad region 26. Once the pads 39 in the I/O pad region 26 are bumped, the flex carrier 44 (FIG. 7) may be attached, as indicated in block 80. In accordance with alternate embodiments, it is also possible to attach the flex cable 44 once the entire sensor assembly 10 has been built.

After the sensor array 12 and the electronics array 14 are bumped and the flex carrier 40 is attached to the I/O pad region 26, the sensor array 12 may be placed on top of the electronics array 14, as indicated in block 82. As will be appreciated, the sensor array 12 and the electronics array 14 are bumped such that the bumps on each array align with bumps on the other array when the arrays are arranged in a flip chip position. Next, the bumps are reflowed, as indicated in block 84, such that each of the bumps on the electronics array 14 and each of the bumps on the sensor array 12 form respective single interconnects from the sensor array 12 to the electronics array 14. This is best illustrated by reference numeral 36 in FIG. 7. Finally, after reflow, the underfill may be applied by using the capillary properties of the liquid underfill materials to completely fill the region between the electronics array 14 and the sensor array 12, as indicated in block 86. In accordance with alternate embodiments, either the sensor array 12 or the electronics array 14 (rather than both) may be bumped and subsequently flip-chip bonded together. Accordingly, steps 74 or 78 may be omitted. Still further, in accordance with another embodiment, it may be advantageous to bump the entire sensor array 12 while bumping only a portion (e.g., the I/O region) of the electronics array 14.

It should also be understood that the modular aspects of the sensor assembly 10, in accordance with various embodiments of the present invention, enables testing at various points during the fabrication process 70. For example, in accordance with the process 70, testing may occur between steps 72 and 74, 76 and 78, 80 and 82 and/or after step 86. The amount of testing and points in the process 70 at which testing is performed will vary depending on the application.

While only certain features of the invention have been illustrated and described herein, many modification and changes will occur to those skilled in the art. It is, therefore, to be understood that the appended claims are intended to cover all such modifications and changes that fall within the true spirit of the invention.

The invention claimed is:

1. A sensor assembly comprising:
   a sensor array comprising a plurality of sensor modules, wherein each of the plurality of sensor modules comprises a plurality of sensor sub-arrays; and
   an electronics array coupled to the sensor array and comprising a plurality of integrated circuit modules, wherein each of the plurality of integrated circuit modules comprises a plurality of integrated circuit chips.

2. The sensor assembly, as set forth in claim 1, wherein the sensor array is coupled to the electronics away via an interconnect.

3. The sensor assembly, as set forth in claim 2, wherein the interconnect comprises one of flip-chip bump bonds, atomic bonds, low temperature fusion bond, laminated gold bumps or indium bumps, copper compression bond, anisotropic conductive films, or combinations thereof.

4. The sensor assembly, as set forth in claim 1, wherein each of the sensor sub-arrays comprises one of a capacitive micromachined ultrasonic transducer (cMUT), a Cadmium Zinc Telluride (CZT) sensor, a piezoelectric transducer (PZT), a piezoelectric micro machined ultrasonic transducer (PMUT), or a photosensor array.

5. The sensor assembly, as set forth in claim 1, wherein each of the plurality of integrated circuit chips comprises an input/output pad region arranged along a single edge of the integrated circuit chip and configured to couple the integrated circuit chip to a sensor system.

6. The sensor assembly, as set forth in claim 1, wherein each of the plurality of integrated circuit chips comprises an input/output pad region arranged along more than one edge of the integrated circuit chip and configured to couple the integrated circuit chip to an ultrasound system.

7. The sensor assembly, as set forth in claim 1, wherein each of the plurality of sensor sub-arrays comprises an input/output pad region arranged along a single edge of the integrated circuit chip and configured to couple the integrated circuit chip to an ultrasound system.

8. The sensor assembly, as set forth in claim 7, wherein each of the plurality of integrated circuit chips comprises an input/output pad region, wherein the input/output pad region is electrically coupled to a substrate via bondwires.

9. The sensor assembly, as set forth in claim 1, wherein the sensor array is coupled to a first side of the electronics array, and wherein the sensor assembly further comprises a substrate coupled to a second side of the electronics array, opposite the first side.

10. The sensor assembly, as set forth in claim 1, wherein the sensor array is coupled to a first side of the electronics array, and wherein the sensor assembly further comprises a second electronics away coupled to a second side of the electronics array, opposite the first side.

11. The sensor assembly, as set forth in claim 10, further comprising a substrate coupled to a second side of the second electronics array, opposite the electronics array, wherein each of the electronics array and the second electronics away are electrically coupled to the substrate via bondwires.

12. The sensor assembly, as set forth in claim 1, wherein one of the sensor away or the electronics away or both includes a redistribution layer (RDL).

13. The sensor assembly, as set forth in claim 1, wherein each of the plurality of sensor sub-array comprises a plurality of sensor elements arranged on a topside of a wafer, and wherein the wafer comprises through-wafer vias configured to electrically couple the plurality of sensor elements to pads arranged on a backside of the wafer.

14. The sensor assembly, as set forth in claim 1, wherein each of the plurality of sensor modules comprises a first number of sensor sub-arrays, and wherein each of the plurality of integrated circuit modules comprises a second number of integrated circuit chips, wherein the first number is equal to the second number.

15. The sensor assembly, as set forth in claim 1, wherein each of the plurality of sensor modules comprises two or more sensor sub-arrays.

16. The sensor assembly, as set forth in claim 1, wherein the sensor array is stacked on top of the electronics array.

17. The sensor assembly, as set forth in claim 1, wherein a ratio of sensor modules to integrated circuit modules is 1:1.

18. The sensor assembly, as set forth in claim 1, wherein a ratio of sensor sub-arrays to integrated circuit chips is 1:1.

19. The sensor assembly, as set forth in claim 1, wherein each of the plurality of integrated circuit chips is configured to control a respective one of the plurality of sensor sub-arrays.

20. The sensor assembly, as set forth in claim 1, further comprising an interconnect configured to couple the sensor array to the electronics array, wherein the interconnect comprises a plurality of conductive bumps configured to mechanically couple the sensor away to the electronics array and to transmit electrical signals between the sensor array and the electronics array.

21. The sensor assembly, as set forth in claim 20, wherein the plurality of conductive bumps are surrounded by an underfill material disposed between the sensor away and the electronics array.

22. The sensor assembly, as set forth in claim 21, wherein the underfill material comprises materials configured to acoustically enhance the performance of the sensor array.

* * * * *

UNITED STATES PATENT AND TRADEMARK OFFICE
CERTIFICATE OF CORRECTION

PATENT NO. : 7,451,651 B2
APPLICATION NO. : 11/636822
DATED : November 18, 2008
INVENTOR(S) : Woychik et al.

It is certified that error appears in the above-identified patent and that said Letters Patent is hereby corrected as shown below:

In Column 9, Line 2, delete "FIG. 1," and insert -- FIG. 11, --, therefor.

In Column 10, Line 63, in Claim 2, delete "away" and insert -- array --, therefor.

In Column 11, Line 36, in Claim 10, delete "away" and insert -- array --, therefor.

In Column 11, Line 41, in Claim 11, delete "away" and insert -- array --, therefor.

In Column 12, Line 2, in Claim 12, after "sensor" delete "away" and insert -- array --, therefor.

In Column 12, Line 2, in Claim 12, after "electronics" delete "away" and insert -- array --, therefor.

In Column 12, Line 5, in Claim 13, delete "sub-array" and insert -- sub-arrays --, therefor.

In Column 12, Line 32, in Claim 20, delete "away" and insert -- array --, therefor.

In Column 12, Line 37, in Claim 21, delete "away" and insert -- array --, therefor.

Signed and Sealed this

Thirtieth Day of November, 2010

David J. Kappos
*Director of the United States Patent and Trademark Office*